(12) United States Patent
Boyle et al.

(10) Patent No.: US 7,572,802 B2
(45) Date of Patent: Aug. 11, 2009

(54) 7-[2-[4-(6-FLUORO-3-METHYL-1,2-BENZISOXAZOL-5-YL)-1-PIPERAZINYL]ETHYL]-2-(1-PROPYNYL)-7H-PYRAZOLO-[4,3-E]-[1,2,4]-TRIAZOLO-[1,5-C]-PYRIMIDIN-5-AMINE

(75) Inventors: Craig D. Boyle, Branchburg, NJ (US); Samuel Chackalamannil, Califon, NJ (US); Unmesh Shah, Green Brook, NJ (US); Jean E. Lachowicz, Berkeley Heights, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/525,065

(22) Filed: Sep. 21, 2006

(65) Prior Publication Data
US 2007/0072867 A1   Mar. 29, 2007

Related U.S. Application Data

(60) Provisional application No. 60/720,027, filed on Sep. 23, 2005.

(51) Int. Cl.
*A61K 31/505* (2006.01)
*C07D 239/00* (2006.01)
*C07D 471/00* (2006.01)
*C07D 487/00* (2006.01)
*C07D 491/00* (2006.01)

(52) U.S. Cl. ...................................... 514/267; 544/251
(58) Field of Classification Search ............ 514/255.05, 514/252.16; 544/251
See application file for complete search history.

(56) References Cited

U.S. PATENT DOCUMENTS

| 5,565,460 | A | 10/1996 | Suzuki et al. | |
|---|---|---|---|---|
| 6,630,475 | B2 | 10/2003 | Neustadt et al. | |
| 6,653,315 | B2 | 11/2003 | Tulshian et al. | |
| 6,897,217 | B2 * | 5/2005 | Neustadt et al. | 514/252.16 |
| 2002/0099061 | A1 | 7/2002 | Neustadt et al. | |
| 2004/0138235 | A1 | 7/2004 | Grezlak et al. | |
| 2004/0220194 | A1 * | 11/2004 | Neustadt et al. | 514/252.16 |
| 2005/0222164 | A1 * | 10/2005 | Neustadt et al. | 514/252.16 |

FOREIGN PATENT DOCUMENTS

| WO | WO 95/01356 | 1/1995 |
|---|---|---|
| WO | WO 97/05138 | 2/1997 |
| WO | WO 98/52568 | 11/1998 |
| WO | WO 01/92264 | 12/2001 |
| WO | WO 02/055083 | 7/2002 |
| WO | WO 03/032996 | 4/2003 |
| WO | WO 2005/044245 | 5/2005 |
| WO | WO 2005/103055 | 11/2005 |

OTHER PUBLICATIONS

Pinna, et al., New Therapies for the treatment of Parkinson's disease: Adenosine A2A receptor Antagonists, Life Sciences, 77, 3259-67 (2005).*
Layzer, Degenerative Diseases of the Nervous System, Cecil Textbook of Medicine, 20th edition (1996), vol. 2, pp. 2050-2057.*
Damasio, Alzheimer's Disease and Related Dementias, Cecil Textbook of Medicine, 20th edition (1996), vol. 2, pp. 1992-1996.*
Ongini et al., PubMed Abstract (Ann NY Acad. Sci. 825:30-48), Oct. 1997.*
Aiba et al., Total Synthesis and Antifungal Activity of 9-Methoxystrobilurin L as the Originally Proposed 1,4-Benzodioxan Structure, *Bioorg. Med. Chem.* Lett., 11 (2001), 2783-2786.
Baraldi et al., Synthesis of New Pyrazolo[4,3-e]1,2,4-Triazolo[1,5-c] Pyrimidine and 1,2,3-Triazolo[4,5-e]1,2,4-Triazolo[1,5-c]Pyrimidine Displaying Potent and Selective Activity as $A2_a$ Adenosine Receptor Antagonists, *Bioorganic and Med. Chem. Let.* 4(21) (1994) 2539-2544.
Baraldi et al., Pyrazolo[4,3-*e*]-1,2,4-triazolo[1,5-*c*]pyrimidine Derivatives: Potent and Selective $A2_A$ Adenosine Antagonists, *J. Med. Chem.* 39 (1996), 1164-1171.
Baraldi et al., Pyrazolo[4,3-e]1,2,4-triazolo[1,5-c]pyrimidine Derivatives as Highly Potent and Selective Human $A_3$ Adenosine Receptor Antagonists: Influence of the Chain at the $N^8$ Pyrazole Nitrogen, *J. Med. Chem.*, 43 (2000) 4768-4780.
Baum et al., Synthesis of Electron-Deficient Oxetanes. 3-Azidooxetane, 3-Nitrooxetane, and 3,3-Dinitrooxetane, *J. Org. Chem.* 48 (1983), 2953-2956.
Cornelius et al., A Convenient Synthesis of Mono- and Polyhalogenated Benzocyclanones, *Synth. Commun.*, 24, (19) (1994), 2777-2788.
Damasio, Alzheimer's Disease and related Dementias, Cecil Textbook of Medicine, 20th Ed., vol. 2, p. 1992-1996 (1996).
Huang et al., Magnesium Bromide Promoted Barbier-Type Intramolecular Cyclization of Halo-Substituted Acetals, Ketals,and Orthoesters, *Tet. Lett.*, 40 (1999), 8647-8650.
Kanth et al., Selective Reduction of Carboxylic Acids into Alcohols Using $NaBH_4$ and $I_2$, *J. Org. Chem.*, 56 (1991), 5964-5965.

(Continued)

*Primary Examiner*—James O Wilson
*Assistant Examiner*—Erich A Leeser
(74) *Attorney, Agent, or Firm*—Krishna G. Banerjee

(57) ABSTRACT

The compound having the structural formula I

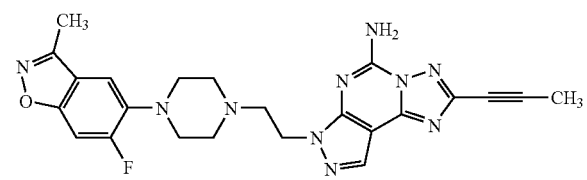

or a pharmaceutically acceptable salt thereof, is disclosed, as well as its use in the treatment of central nervous system diseases, in particular Parkinson's disease, Extra Pyramidal Syndrome, restless legs syndrome and attention deficit hyperactivity disorder, pharmaceutical compositions comprising it, and combinations with other agents.

15 Claims, No Drawings

OTHER PUBLICATIONS

Layzer et al., Degenerative Disease of the Nervous System, Cecil Textbook of Medicine, 20th Ed., vol. 2, p. 2050-2057, (1996).

Lee et al., Facile Synthesis of Oxazoles Starting from Ketones, *Synth. Commun.*, 33, (9) (2003), 1611-1614.

Merck.com, Periodic Limb Movement Disorder and Rest Syndrome (RLS), Neurologic Disorders, Sleep and Wakefulness Disorders, (2007).

Merck Manual Fifteenth Edition, Neurologic Disorders (1987), 1420-1421.

Ongini et al., Adenosine $A2_A$ Receptors and Neuroprotection, *Schering-Plough Research Institute San Raffaele Science Park Via Olgettina 58 I-20132* Milan, Italy, 30-40.

Orito et al., Synthesis of 5-Iodobenzofurans and 6-Iodobenzopyrans via Direct Iodination with Mercury (II) Oxide-Iodine Reagent, *Synthesis*, 23 (1997), 23-25.

Pinna et al., New Therapies for the treatment of Parkinson's disease: Adenosine A2A receptor Antagonists, *Life Sciences*, 77, 3259-67 (2005).

Popoli et al., Blockade of Striatal Adenosine $A2_A$ Receptor Reduces, through a Presynaptic Mechanism, Quinolinic Acid-Induced Excitotoxicity: Possible Relevance to Neuroprotective Interventions in Neurodegenerative Diseases of the Straitum, *The Journal of Neuroscience*, 22(5) (2002) 1967-1975.

Rao et al., Parkinson's Disease: Diagnosis and Treatment, *American Family Physician*, 74 (12), (2006), 2046-2054.

Roche, Bioreversible Carriers in Drug Design, American *Pharmaceutical Association and Pergamon Press* (1987).

Saletu et al., Sleep Laboratory Studies in Restless Legs Syndrome Patients as Compared with Normals and acute Effects of Ropinirole, *Neuropsychobiology*, 41 (4), (2000), 190-199.

T. Higuchi and V. Stella, Pro-drugs as Novel Delivery Systems, 14 (1987).

Trenkwalder et al., The Restless Legs Syndrome, Neurology. thelancet.com, 4 (2005) 465-475.

Ungerstedt et al., Quantitative recording of rotational behavior in rats after 6-hydroxy-dopamine lesions of the nigrostriatal dopamine system, *Brain Research*, 24 (1970), 485-493 Abstract.

Ungerstedt et al., 6-hydroxy-dopamine induced degeneration of central monoamine neurons, *Eur. J. Pharmacol.*, 5 (1968), 107-110 Abstract.

Varelis et al., Preparation of Optically Active (S)-2-(Benzyloxy)propanal, *Aust. J. Chem.*, 48 (1995), 1775-1779.

Weiden, PJ, EPS Profiles: the atypical antipsychotics are not all the same, *PubMed, J.. Psychiatr Pract.* 13 (1), (2007),13-24 Abstract.

Yacoubi et al., Adenosine $A2_A$ receptors and depression, *Neurology*, 61 (Suppl 6), (2003), S82-S87.

Yacoubi et al., Adenosine $A2_A$ receptor antagonists are potential antidepressants: evidence based on pharmacology and $A2_A$ receptor knockout mice, *British Journal of Pharmacology*, 134 (2001), 68-77.

* cited by examiner

7-[2-[4-(6-FLUORO-3-METHYL-1,2-BENZISOXAZOL-5-YL)-1-PIPERAZINYL]ETHYL]-2-(1-PROPYNYL)-7H-PYRAZOLO-[4,3-E]-[1,2,4]-TRIAZOLO-[1,5-C]-PYRIMIDIN-5-AMINE

This Application claims the benefit of U.S. Provisional Application No. 60/720,027 filed Sep. 23, 2005.

FIELD OF THE INVENTION

The present invention relates to 7-[2-[4-(6-fluoro-3-methyl-1,2-benzisoxazol-5-yl)-1-piperazinyl]ethyl]-2-(1-propynyl)-7H-pyrazolo-[4,3-e]-[1,2,4]-triazolo[1,5-c]pyrimidin-5-amine, an adenosine $A_{2a}$ receptor antagonist, the use of said compound in the treatment of central nervous system disorders including movement disorders, e.g., Parkinson's Disease, Extra-Pyramidal Syndrome, restless legs syndrome, essential tremor and Huntington's Disease; attention disorders, e.g., attention deficit hyperactivity disorder, cognitive impairment and negative symptoms of schizophrenia; and to other central nervous system diseases such as depression, stroke and psychoses. The invention also relates to pharmaceutical compositions comprising said compound.

BACKGROUND

Adenosine is known to be an endogenous modulator of numerous physiological functions. At the cardiovascular system level, adenosine is a strong vasodilator and a cardiac depressor. In the central nervous system, adenosine induces sedative, anxiolytic and antiepileptic effects. In the respiratory system, adenosine induces bronchoconstriction. In the renal system, it exerts a biphasic action, inducing vasoconstriction at low concentrations and vasodilation at high doses. Adenosine acts as a lipolysis inhibitor on fat cells and as an antiaggregant on platelets.

Adenosine action is mediated by the interaction with different membrane specific receptors which belong to the family of receptors coupled with G proteins. Biochemical and pharmacological studies, together with advances in molecular biology, have allowed the identification of at least four subtypes of adenosine receptors: $A_1$, $A_{2a}$, $A_{2b}$ and $A_3$. $A_1$ and $A_3$ receptors inhibit, while $A_{2a}$ and $A_{2b}$ receptors stimulate the activity of the enzyme adenylate cyclase. Analogs of adenosine able to interact as antagonists with the $A_1$, $A_{2a}$, $A_{2b}$ and $A_3$ receptors have also been identified.

Selective antagonists for the $A_{2a}$ receptor are of pharmacological interest because of their reduced probability of potentiating side effects. In the central nervous system, $A_{2a}$ antagonists can have antidepressant properties and stimulate cognitive functions. Moreover, data has shown that $A_{2a}$ receptors are present in high density in the basal ganglia, known to be important in the control of movement. Hence, $A_{2a}$ antagonists can improve motor impairment due to neurodegenerative diseases such as Parkinson's disease, senile dementia as in Alzheimer's disease, and psychoses.

Adenosine $A_{2a}$ receptor antagonists have been disclosed as being useful in the treatment or prevention of Extra Pyramidal Syndrome (EPS), dystonia, restless legs syndrome (RLS) or periodic limb movement in sleep (PLMS) in WO 05/044245, and have been disclosed as being useful in the treatment of attention deficit hyperactivity disorder (ADHD) in WO 02/055083.

EPS is a collective term for a series of adverse neurological reactions associated with the use of antipsychotic drugs. There are six different categories of EPS-related neurological syndromes of which four, dystonia, akathisia, pseudoparkinsonism (parkinsonian syndrome), and tardive dyskinesia, are particularly prevalent in patients taking antipsychotic medication. Dystonia is a painful spasm of the muscle groups of, in particular, the neck, jaw, back, pharynx, and larynx. It is most common in young males being treated with antipsychotic drugs, but can also be associated with the use of cocaine, tricyclic antidepressants, lithium and anticonvulsants such as phenytoin and carbamazepine. Pseudoparkinsonism manifests itself as akinesia (rigidity, stiffness and slow voluntary motion, stooped, shuffling walk) and tremor and these symptoms develop within weeks or months after initiation of therapy. Akathisia manifests itself as strong, subjective inner feelings of distress or discomfort characterized by motor restlessness. Often mistaken for agitation or anxiety, this common syndrome is frequently under-diagnosed and is the least responsive to treatment. Tardive dyskinesia is a late-appearing syndrome associated with chronic use of neuroleptic drugs. It occurs more frequently in older patients and is characterized by stereotypical, repetitive, involuntary, quick choreiform movements of the face, eyelids, mouth, tongue, extremities and trunk.

EPS is more prevalent with the use of typical antipsychotic agents but has also been reported with the use of atypical agents. Typical antipsychotics include loxapine, haloperidol, chlorpromazine, prochlorperazine and thiothixene. Atypical antipsychotics include clozapine, olanzapine, loxapine, quetiapine, ziprasidone, risperidone and aripiprazole.

Akathisia is also a characteristic of RLS and PLMS, as well as PLMD (periodic leg (or limb) movement disorder). RLS is a common disorder that causes patients to have an irresistible and unpleasant desire to move their legs; it usually manifests during periods of inactivity and/or at night, and can disturb sleep. Patients who do not have the typical RLS symptoms, but who do exhibit periodic leg movements that adversely impact sleep, are diagnosed with PLMS. Treatments for RLS and PLMS have included levodopa/carbidopa, levodopa/benserazide, dopamine agonists such as pramipexole and ropinerole, benzodiazepines, opioids, anticonvulsants and iron (ferrous sulfate). RLS and PLMS have been extensively described in the literature, for example by Saletu et al, *Neuropsychobiology*, 41, 4 (2000), p. 190-9.

Some xanthine-related compounds have been found to be $A_1$ receptor selective antagonists, and xanthine and non-xanthine compounds have been found to have high $A_{2a}$ affinity with varying degrees of $A_{2a}$ vs. $A_1$ selectivity. Triazolo-pyrimidine adenosine $A_{2a}$ receptor antagonists have been disclosed previously, for example in WO 95/01356; U.S. Pat. No. 5,565,460; WO 97/05138; WO 98/52568, U.S. Pat. No. 6,630,475, U.S. Pat. No. 6,653,315, U.S. Pat. No. 6,897,217 and PCT/US05/013454, filed Apr. 19, 2005.

This invention is a selection invention over U.S. Pat. No. 6,897,217.

SUMMARY OF THE INVENTION

The present invention relates to the compound having the structural formula I

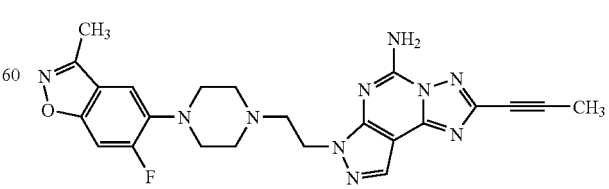

or a pharmaceutically acceptable salt thereof.

Another aspect of the invention is a pharmaceutical composition comprising a therapeutically effective amount of the compound of formula I in a pharmaceutically acceptable carrier.

Yet another aspect of the invention is a method of treating central nervous system disorders including movement disorders, e.g., Parkinson's Disease, Extra-Pyramidal Syndrome, restless legs syndrome, essential tremor, Huntington's Disease, dystonia, periodic limb movement in sleep; attention disorders, e.g., attention deficit hyperactivity disorder, cognitive impairment and negative symptoms of schizophrenia; and to other central nervous system diseases such as depression, stroke and psychoses, comprising administering the compound of formula I to a mammal in need of such treatment.

In particular, the invention is drawn to the method of treating movement disorders such as Parkinson's disease, essential tremor or Huntington's Disease comprising administering the compound of formula I to a mammal in need of such treatment.

Still another aspect of the invention is a method of treating Parkinson's disease with a combination of the compound of formula I and one or more agents useful in the treatment of Parkinson's disease, for example dopamine; L-DOPA; a dopaminergic agonist; an inhibitor of monoamine oxidase, type B (MAO-B); a DOPA decarboxylase inhibitor (DCI); or a catechol-O-methyltransferase (COMT) inhibitor. Also claimed is a pharmaceutical composition comprising the compound of formula I and one or more agents known to be useful in the treatment of Parkinson's in a pharmaceutically acceptable carrier.

The invention also relates to the treatment or prevention of EPS (e.g., dystonia, akathisia, pseudoparkinsonism and tardive dyskinesia) comprising administering the compound of formula I to a mammal in need of such treatment. In particular, this method is for the treatment or prevention of EPS in patients treated with an antipsychotic agent that has the side effect of inducing EPS. The compound of formula I can be administered after the symptoms of EPS have manifested, or the compound of formula I can be administered at the onset of administering an antipsychotic agent in order to prevent EPS from occurring. Thus, the invention also includes a method of treating or preventing EPS induced by an antipsychotic agent comprising administering a combination of an antipsychotic agent and the compound of formula I to a patient in need thereof.

The invention also relates to the treatment of primary (idiopathic) dystonia, and to the treatment or prevention of dystonia in patients who exhibit dystonia as a result of treatment with a tricyclic antidepressant, lithium or an anticonvulsant, or who have used cocaine, comprising administering a therapeutically effective amount of the compound of formula I to a patient in need thereof. When dystonia is caused by treatment with a tricyclic antidepressant, lithium or an anticonvulsant, the compound of formula I can be administered after the symptoms of dystonia have manifested, or the compound of formula I can be administered at the onset of administering a tricyclic antidepressant, lithium or an anticonvulsant in order to prevent dystonia from occurring. The invention, therefore, also includes a method of treating or preventing dystonia induced by a tricyclic antidepressant, lithium or an anticonvulsant comprising administering a combination of the compound of formula I and a tricyclic antidepressant, lithium or an anticonvulsant to a patient in need thereof.

The invention further relates to treatment of abnormal movement disorders such as RLS or PLMS, comprising administering to a patient in need thereof a therapeutically effective amount of the compound of formula I. The invention also comprises a method of treating RLS or PLMS comprising administering a combination of the compound of formula I with another agent useful in treating RLS or PLMS, such as levodopa/carbidopa, levodopa/benserazide, a dopamine agonist, a benzodiazepine, an opioid, an anticonvulsant or iron, to a patient in need thereof.

The invention also relates to the treatment of attention related disorders such as attention deficit disorder (ADD) and ADHD, as well as cognitive impairment and negative symptoms of schizophrenia, comprising administering a therapeutically effective amount of the compound of formula I.

In another aspect, this invention relates to a kit comprising, in separate containers in a single package, pharmaceutical compositions for use in combination to treat Parkinson's Disease, wherein one container comprises a pharmaceutical composition comprising an effective amount of the compound of formula I in a pharmaceutically acceptable carrier, and wherein a separate container comprises a pharmaceutical composition comprising an effective amount of an agent useful in the treatment of Parkinson's disease.

In another aspect, this invention relates to a kit comprising, in separate containers in a single package, pharmaceutical compositions for use in combination to treat or prevent EPS caused by treatment with antipsychotic agent, wherein one container comprises a pharmaceutical composition comprising an effective amount of the compound of formula I in a pharmaceutically acceptable carrier, and wherein a separate container comprises a pharmaceutical composition comprising an effective amount of an antipsychotic agent.

In another aspect, this invention relates to a kit comprising, in separate containers in a single package, pharmaceutical compositions for use in combination to treat or prevent dystonia caused by treatment with a tricyclic antidepressant, lithium or an anticonvulsant, wherein one container comprises a pharmaceutical composition comprising an effective amount of the compound of formula I in a pharmaceutically acceptable carrier, and wherein a separate container comprises a pharmaceutical composition comprising an effective amount of a tricyclic antidepressant, lithium or an anticonvulsant.

In another aspect, this invention relates to a kit comprising, in separate containers in a single package, pharmaceutical compositions for use in combination to treat RLS or PLMS, wherein one container comprises a pharmaceutical composition comprising an effective amount of the compound of formula I in a pharmaceutically acceptable carrier, and wherein a separate container comprises a pharmaceutical composition comprising an effective amount of levodopa/carbidopa, levodopa/benserazide, a dopamine agonist, a benzodiazepine, an opioid, an anticonvulsant or iron.

The invention also relates to the use of the compound of formula I for the preparation of a medicament for treating or preventing Parkinson's Disease, EPS, dystonia, RLS, PLMS, essential tremor, Huntington's Disease, cognitive impairment or negative symptoms of schizophrenia, alone or in combination with the other agents discussed above.

DETAILED DESCRIPTION

As used herein, the term "composition" is intended to encompass a product comprising the specified ingredients in the specified amounts, as well as any product which results, directly or indirectly, from combination of the specified ingredients in the specified amounts.

Prodrugs and solvates of the compound of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Prodrugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Polymorphic forms of the compound of formula I, and of the salts, solvates and prodrugs of the compound of formula I, are intended to be included in the present invention.

"Effective amount" or "therapeutically effective amount" is meant to describe an amount of compound or a composition of the present invention effective as an adenosine $A_{2a}$ receptor antagonist and thus producing the desired therapeutic effect in a suitable patient.

"Patient" includes both human and animals.

"Mammal" means humans and other mammalian animals.

The compound of formula I forms salts that are also within the scope of this invention. Reference to the compound of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when the compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting the compound of formula I with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartrates, thiocyanates, toluenesulfonates (also known as tosylates) undecanoates, and the like. Additionally, acids which are generally considered suitable for the formation of pharmaceutically useful salts from basic pharmaceutical compounds are known.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydro-abietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compound (including those of the salts, solvates and prodrugs of the compound as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

The other agents known to be useful in the treatment of Parkinson's disease that can be administered in combination with the compounds of formula I include: L-DOPA; dopaminergic agonists such as quinpirole, ropinirole, pramipexole, pergolide and bromocriptine; MAO-B inhibitors such as deprenyl and selegiline; DOPA decarboxylase inhibitors such as carbidopa and benserazide; and COMT inhibitors such as tolcapone and entacapone.

Antipsychotic agents causing the EPS treated by adenosine $A_{2a}$ receptor antagonists and for use in combination with adenosine $A_{2a}$ receptor antagonists include typical and atypical antipsychotic agents. Typical antipsychotics include loxapine, haloperidol, chlorpromazine, prochlorperazine and thiothixene. Atypical antipsychotics include clozapine, olanzapine, loxapine, quetiapine, ziprasidone, risperidone and aripiprazole.

Tricyclic antidepressants causing dystonia treated by adenosine $A_{2a}$ receptor antagonists include perphenazine, amitriptyline, desipramine, doxepin, trimipramine and protriptyline. Anticonvulsants which may cause dystonia, but which also may be useful in treating ERLS or PLMS include phenytoin, carbamazepine and gabapentin.

Dopamine agonists useful in treating RLS and PLMS include pergolide, pramipexole, ropinerole, fenoldopam and cabergoline.

Opioids useful in treating PRLS and PLMS include codeine, hydrocodone, oxycodone, propoxyphene and tramadol.

Benzodiazepines useful in treating PRLS and PLMS include clonazepam, triazolam and temazepam.

The antipsychotics, tricyclic antidepressants, anticonvulsants, dopamine agonists, opioids and benzodiazepines are commercially available and are described in the literature, e.g., in The Physicians' Desk Reference (Montvale: Medical Economics Co., Inc., 2001).

It is contemplated that the compound of formula I could be administered in combination with one or more other agents (e.g., antipsychotics, tricyclic antidepressants, anticonvulsants, dopamine agonists, opioids or benzodiazepines), although administration of the compound of formula I in combination with one other agent is preferred for each of the indications. While administration of separate dosage forms of the compound of formula I and the other agent(s) are preferred, it is also contemplated that the other agent(s) could be combined in a single dosage form with the compound of formula I for the treatment or prevention of Parkinson's disease, EPS, dystonia, RLS or PLMS. It is also contemplated that the compound of formula I could be administered in combination with another adenosine $A_{2a}$ antagonist.

Compounds of formula I can be prepared by known methods from starting materials either known in the art or prepared by methods known in the art; see, for example, U.S. Pat. No. 6,897,217.

Abbreviations used in the specification are as follows: Ac (acetyl); Me (methyl); Et (ethyl); Ph (phenyl); DMF (dimethylformamide); DIPEA (diisopropylethylamine); RT (room temperature).

EXAMPLE 1

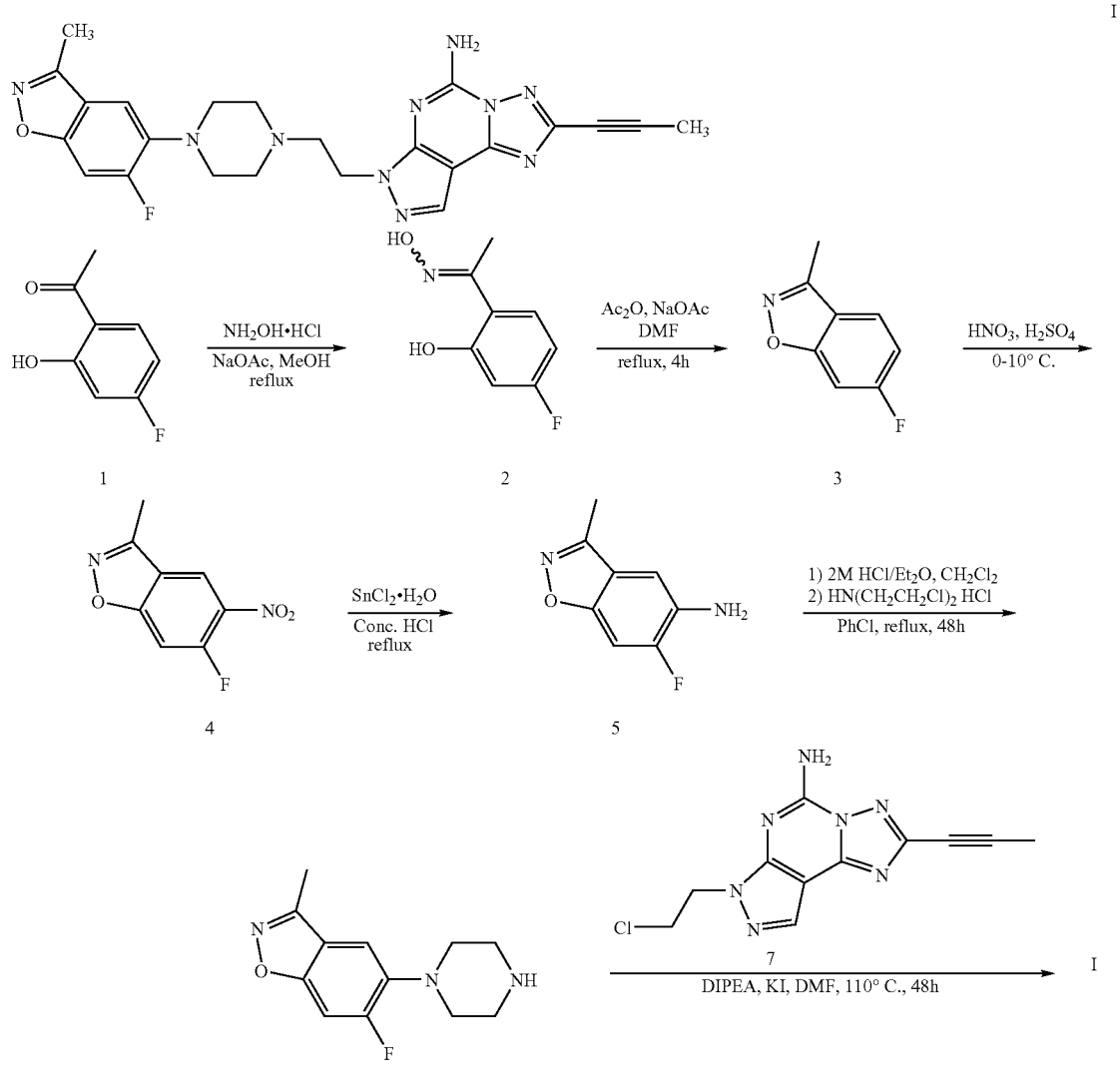

Step 1: A mixture of 4-fluoro-2-hydroxyacetophenone 1 (50 g, 324 mmol), hydroxylamine hydrochloride (45 g, 648 mmol), and sodium acetate (40 g, 488 mmol) in anhydrous MeOH (1 L) was refluxed for 2 h. After cooling to RT, the reaction mixture was slowly poured onto ice and stirred for 30 min. The white precipitate thus obtained was filtered through suction and then dissolved in $CH_2Cl_2$, dried ($MgSO_4$), filtered, and concentrated to give 2 as a white solid (50 g, 91% yield) which was used without further purification for the next step.

Step 2: To a solution of the oxime 2 (50 g, 296 mmol) in DMF (800 ml) was added sodium acetate (55 g, 670 mmol) followed by acetic anhydride (65 ml, 689 mmol). The reaction mixture was refluxed for 3-4 h, at which stage all the starting material was consumed as indicated by TLC (10% EtOAc in hexanes). After cooling to RT, the reaction mixture was poured into water and extracted several times with ether. The combined organic fractions were washed with brine, dried ($Na_2SO_4$), filtered and concentrated to give 3 as a brownish solid (42 g, 94% yield).

Step 3: To an ice-cold solution of 3 (42 g, 278 mmol) in conc. $H_2SO_4$ (300 ml) was added dropwise conc. $HNO_3$ (70 ml) through an addition funnel. After the addition was complete, the reaction mixture was warmed to RT and stirred for 2-3 h. After the starting material was consumed as indicated by TLC (10% EtOAc in hexanes), the reaction mixture was poured slowly on ice with constant shaking. The resulting solid was filtered, dissolved in $CH_2Cl_2$ and washed with saturated aq. $NaHCO_3$ solution and brine. The combined organic fractions were dried over $MgSO_4$, filtered, and concentrated to give 47 g (86% yield) of 4 as a yellow solid.

Step 4: A solution of 4 (47 g, 240 mmol) in ACOH (800 ml) was warmed to 40° C. and to this warm solution was added a solution of $SnCl_2.H_2O$ (150 g, 665 mmol) in conc. HCl (400 ml). The reaction mixture was refluxed for 2 h and then cooled to RT. The pH was carefully adjusted to 5-6 with aqueous NaOH to precipitate most of the tin salts and then ether was added to the mixture with constant stirring. After decanting the liquid, the organic layer was separated and the aqueous layer was back extracted several times with ether. The combined organic fractions were washed with brine, dried ($Na_2SO_4$), filtered and concentrated to give a brown oil. Purification by column chromatography (10-20% EtOAc in hexanes) gave 22 g (55% yield) of 5 as a yellow solid.

Step 5: A solution of 5 (3.2 g, 19 mmol) in $CH_2Cl_2$ (100 ml) was treated with 2M HCl/ether (9.6 ml, 19 mmol) and the solvent was removed under reduced pressure. The white solid was taken in chlorobenzene (80 ml) and treated with bis(chloroethyl)-amine (3.8 g, 21 mmol). The reaction mixture was refluxed for 48 h, at which stage most of the starting material was consumed. Most of the solvent was removed under reduced pressure and the residue was taken up in hot MeOH (200 ml). The black insoluble residue was filtered off and the filtrate was purified by column chromatography (2-5% 7N $NH_3$-MeOH in $CH_2Cl_2$) to give 2.6 g (57% yield) of 6.

Step 6: A mixture of 6 (2.6 g, 11 mmol), 7 (3.2 g, 12 mmol), KI (2.0 g, 12 mmol), and DIPEA (2.3 ml, 13.3 mmol) in DMF (30 ml) was heated at 110° C. for 48 h. After cooling to RT, water was added and the resulting solid was filtered. The solid residue was dissolved in 10% MeOH-$CH_2Cl_2$, dry loaded on a silica gel column, and purified (2% MeOH in $CH_2Cl_2$) giving 2.7 g (52% yield) of the title compound. LCMS: 475 (M+H), purity=100%.

Because of its adenosine $A_{2a}$ receptor antagonist activity, the compound of the present invention is useful in the treatment of central nervous system diseases such as Parkinson's Disease, Extra-Pyramidal Syndrome, restless legs syndrome, essential tremor, Huntington's Disease, attention deficit hyperactivity disorder, cognitive impairment, negative symptoms of schizophrenia, depression, stroke or psychoses. In particular, the compound of the present invention can improve motor-impairment due to neurodegenerative diseases such as Parkinson's disease.

The pharmacological activity of the compound of the invention was determined by the following in vitro and in vivo assays to measure $A_{2a}$ receptor activity.

Human Adenosine $A_{2a}$ and $A_1$ Receptor Competition Binding Assay Protocol

Membrane Sources:

$A_{2a}$: Human $A_{2a}$ Adenosine Receptor membranes, Catalog #RBHA2AM, Perkin Elmer Life Sciences, Shelton Conn. Dilute to 17 µg/100 µl in membrane dilution buffer (see below).

Assay Buffers:

Membrane dilution buffer: Dulbecco's Phosphate Buffered Saline (Gibco/BRL)+10 mM $MgCl_2$.

Compound Dilution Buffer: Dulbecco's Phosphate Buffered Saline (Gibco/BRL)+10 mM $MgCl_2$ supplemented with 1.6 mg/ml methyl cellulose and 16% DMSO. Prepared fresh daily.

Ligands:

$A_{2a}$: [3H]-SCH 58261, custom synthesis, AmershamPharmacia Biotech, Piscataway, N.J. Stock is prepared at 1 nM in membrane dilution buffer. Final assay concentration is 0.5 nM.

$A_1$: [3H]-DPCPX, AmershamPharmacia Biotech, Piscataway, N.J. Stock is prepared at 2 nM in membrane dilution buffer. Final assay concentration is 1 nM.

Non-specific Binding:

$A_{2a}$: To determine non-specific binding, add 100 nM CGS 15923 (RBI, Natick, Mass.). Working stock is prepared at 400 nM in compound dilution buffer.

$A_1$: To determine non-specific binding, add 100 µM NECA (RBI, Natick, Mass.). Working stock is prepared at 400 µM in compound dilution buffer.

Compound Dilution:

Prepare 1 mM stock solutions of compounds in 100% DMSO. Dilute in compound dilution buffer. Test at 10 concentrations ranging from 3 µM to 30 pM. Prepare working solutions at 4× final concentration in compound dilution buffer.

Assay Procedure:

Perform assays in deep well 96 well plates. Total assay volume is 200 µl. Add 50 µl compound dilution buffer (total ligand binding) or 50 µl CGS 15923 working solution ($A_{2a}$ non-specific binding) or 50 µl NECA working solution ($A_1$ non-specific binding) or 50 µl of drug working solution. Add 50 µl ligand stock ([3H]-SCH 58261 for $A_{2a}$, [3H]-DPCPX for $A_1$). Add 100 µl of diluted membranes containing the appropriate receptor. Mix. Incubate at room temperature for 90 minutes. Harvest using a Brandel cell harvester onto Packard GF/B filter plates. Add 45 µl. Microscint 20 (Packard), and count using the Packard TopCount Microscintillation Counter. Determine $IC_{50}$ values by fitting the displacement curves using an iterative curve fitting program (Excel). Determine $K_i$ values using the Cheng-Prusoff equation.

Haloperidol-induced Catalepsy in the Rat

Male Sprague-Dawley rats (Charles River, Calco, Italy) weighing 175-200 g are used. The cataleptic state is induced by the subcutaneous administration of the dopamine receptor antagonist haloperidol (1 mg/kg, sc), 90 min before testing the animals on the vertical grid test. For this test, the rats are placed on the wire mesh cover of a 25×43 plexiglass cage placed at an angle of about 70 degrees with the bench table. The rat is placed on the grid with all four legs abducted and extended ("frog posture"). The use of such an unnatural posture is essential for the specificity of this test for catalepsy. The time span from placement of the paws until the first complete removal of one paw (descent latency) is measured maximally for 120 sec.

The selective $A_{2A}$ adenosine antagonists under evaluation are administered orally at doses ranging between 0.03 and 3 mg/kg, 1 and 4 h before scoring the animals.

In separate experiments, the anticataleptic effects of the reference compound, L-DOPA (25, 50 and 100 mg/kg, ip), were determined.

6-OHDA Lesion of the Middle Forebrain Bundle in Rats

Adult male Sprague-Dowley rats (Charles River, Calco, Como, Italy), weighing 275-300 g, are used in all experiments. The rats are housed in groups of 4 per cage, with free access to food and water, under controlled temperature and 12 hour light/dark cycle. The day before the surgery the rats are fasted over night with water ad libitum.

Unilateral 6-hydroxydopamine (6-OHDA) lesion of the middle forebrain bundle is performed according to the method described by Ungerstedt et al. (*Brain Research*, 1971, 6-OHDA and Cathecolamine Neurons, North Holland, Amsterdam, 101-127), with minor changes. Briefly, the animals are anaesthetized with chloral hydrate (400 mg/kg, ip) and treated with desipramine (10 mpk, ip) 30 min prior to 6-OHDA injection in order to block the uptake of the toxin by the noradrenergic terminals. Then, the animals are placed in a stereotaxic frame. The skin over the skull is reflected and the stereotaxic coordinates (−2.2 posterior from bregma (AP), +1.5 lateral from bregma (ML), 7.8 ventral from dura (DV) are taken, according to the atlas of Pellegrino et al (Pellegrino L. J., Pellegrino A. S. and Cushman A. J., *A Stereotaxic Atlas of the Rat Brain*, 1979, New York: Plenum Press). A burr hole is then placed in the skull over the lesion site and a needle, attached to a Hamilton syringe, is lowered into the left MFB. Then 8 μg 6-OHDA-HCl is dissolved in 4 μl of saline with 0.05% ascorbic acid as antioxidant, and infused at the constant flow rate of 1 μl/1 min using an infusion pump. The needle is withdrawn after additional 5 min and the surgical wound is closed and the animals left to recover for 2 weeks.

Two weeks after the lesion the rats are administered with L-DOPA (50 mg/kg, ip) plus Benserazide (25 mg/kg, ip) and selected on the basis of the number of full contralateral turns quantified in the 2 h testing period by automated rotameters (priming test). Any rat not showing at least 200 complete turns/2 h is not included in the study.

Selected rats receive the test drug 3 days after the priming test (maximal dopamine receptor supersensitivity). The new $A_{2A}$ receptor antagonist is administered orally at dose levels ranging between 0.1 and 3 mg/kg at different time points (i.e., 1, 6, 12 h) before the injection of a subthreshold dose of L-DOPA (4 mpk, ip) plus benserazide (4 mpk, ip) and the evaluation of turning behavior.

EPS Assay

The following procedure describes the use of an adenosine $A_{2a}$ antagonist to attenuate the Extra-Pyramidal Syndrome (EPS) displayed in *cebus apella* monkeys sensitized to the dopamine $D_2$ receptor antagonist, haloperidol.

A colony of *Cebus apella* monkeys previously sensitized to the chronic effects of haloperidol exhibits EPS when administered haloperidol acutely (0.3 mg/kg, p.o.). A test compound is administered orally (p.o.) at a dose ranging from 0.3-30 mg/kg, in conjunction with haloperidol. The studies are conducted using a within-subjects design such that each monkey receives all treatments (vehicle and doses of test compound) in a crossover, balanced design. The reduction in the maximum EPS score, as well as the dose-dependent delay in the onset of EPS are determined.

Clinical guidelines for the treatment of RLS and PLMS have been established: see A. L. Chesson et al, *Sleep*, 22, 7 (1999), p. 961-8. Efficacy of adenosine $A_{2a}$ antagonists in treating RLS and PLMS can be determined by a method analogous to the clinical method described in the literature for pramipexole and ropinerole by Weimerskirch et al, *Annals of Pharmacotherapy*, 35, 5 (2001), p. 627-30.

Using the above test procedures, the following results were obtained for the compound of the invention.

Results of the binding assay on the compound of the invention showed an $A_{2a}$ $K_i$ value of 0.43 nM.

Selectivity is determined by dividing $K_i$ for $A_1$ receptor by $K_i$ for $A_{2a}$ receptor. The compound of the invention has a selectivity greater than 2500 fold.

In the 6-OHDA lesion test, test animals administered a combination of a compound of formula I and a sub-threshold amount of L-DOPA demonstrated significantly higher contralateral turning:

L-DOPA: 171±47 rotations
0.1 mpk: 218±142 rotations
0.3 mpk: 406±167 rotations
1 mpk: 360±178 rotations
3 mpk: 403±125 rotations In the haloperidol-induced catalepsy assay in rats @ 4 h, the % inhibition was as follows:

0.3 mpk: 28% inhibition of catalepsy
1 mpk: 47% inhibition of catalepsy
3 mpk: 53% inhibition of catalepsy In the EPS assay, four haloperidol-sensitized monkeys were co-administered the compound of formula I (30 mg/kg) and haloperidol (0.3 mg/kg) in a banana. A scoring system to rate the severity of each symptom was employed over a 6 hour observation period. The compound of formula I completely blocked haloperidol-induced EPS in three subjects during the 6 hr observation period and in the fourth subject, delayed onset and reduced severity of EPS compared to that observed in monkeys dosed with haloperidol alone.

Ex vivo Binding Study to Show Duration of Receptor Occupancy:

Rats were dosed with 1 mg/kg of the compound of formula I and the compound of formula II (generically disclosed in U.S. Pat. No. 6,897,217)

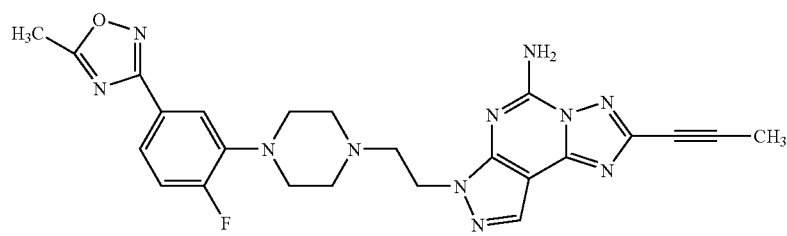

II for 4, 8, 12, and 16 hours prior to sacrifice and removal of brains. The $A_{2a}$ receptor-rich striatal nucleus was dissected and homogenized in buffer solution. Striatal homogenate was incubated with the $A_{2a}$ antagonist radioligand $^3$H-SCH 58261 (see WO 96/38728) prior to separation of bound and free radioactivity by filtration. Bound radioligand on filters was dried, soaked with scintillation fluid, and counted. Homogenates from striata of vehicle-treated rats treated with the same experimental conditions defined the quantity of bound radioligand in the absence of test compound.

For both compounds, receptors are occupied by test compounds at 4 hours, demonstrated by the decrease (42 and 47%) in $^3$H-SCH 58261 binding. However, in striatal homogenates from rats dosed with formula II, radioligand binding is restored to near vehicle-treated levels at 8 hours, indicating that test compound is no longer competing for $A_{2a}$ receptors at that time. The compound of formula I exhibits sustained displacement of radioligand through 12 hours (40% displacement of radiolabel).

For preparing pharmaceutical compositions from the compound of this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compound of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound of formula I in a unit dose of preparation may be varied or adjusted from about 0.1 mg to 1000 mg, more preferably from about 1 mg to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compound of the invention and the pharmaceutically acceptable salts thereof will be regulated according to the judgment of the attending clinician considering such factors as age, condition and size of the patient as well as severity of the symptoms being treated. A typical recommended dosage regimen for the compound of formula I is oral administration of from 10 mg to 2000 mg/day preferably 10 to 1000 mg/day, in two to four divided doses to provide relief from central nervous system diseases such as Parkinson's disease or the other disease or conditions listed above.

The doses and dosage regimen of the other agents used in combination with the compound of formula I, i.e., the Parkinson's Disease agents, the antipsychotics, tricyclcic antidepressants, anticonvulsants, dopamine agonists, benzodiazepines, opioids, lithium or iron, will be determined by the attending clinician in view of the approved doses and dosage regimen in the package insert, taking into consideration the age, sex and condition of the patient and the severity of the disease. When administered in combination, the compound of formula I and the other agent can be administered simultaneously or sequentially. This is particularly useful when the components of the combination are preferably given on different dosing schedules, e.g., one component is administered daily and the other every six hours, or when the preferred pharmaceutical compositions are different, e.g. one is preferably a tablet and one is a capsule. It is therefore advantageous to provide the compound of formula I and the other agent in a kit comprising, in separate containers in a single package, pharmaceutical compositions for use in combination to treat or prevent Parkinson's disease, EPS, dystonia, RLS or PLMS, wherein one container comprises a pharmaceutical composition comprising an effective amount of a compound of formula I in a pharmaceutically acceptable carrier, and wherein a separate container comprises a pharmaceutical composition comprising an effective amount of another agent appropriate to treat the indicated condition.

Those skilled in the art will recognize that a dosage form for one of the components of the combination can be modified to contain both the compound of formula I and another agent, e.g., the compound of formula I and an antipsychotic or the compound of formula I and a dopamine agonist.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A method of treating Parkinson's Disease, Extra-Pyramidal Syndrome, dystonia, akathisia, pseudoparkinsonism, tardive dyskinesia, restless legs syndrome, essential tremor, Huntington's Disease, attention deficit hyperactivity disorder, Alzheimer's Disease, negative symptoms of schizophrenia, depression, stroke or psychoses with a compound of the formula

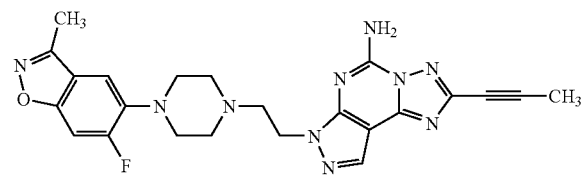

or a pharmaceutically acceptable salt thereof.

2. A method of claim 1 for treating Parkinson's Disease, Extra-Pyramidal Syndrome, restless legs syndrome or attention deficit hyperactivity disorder.

3. A method of treating Parkinson's Disease comprising administering to a mammal in need of such treatment an effective amount of a combination of the compound of the formula

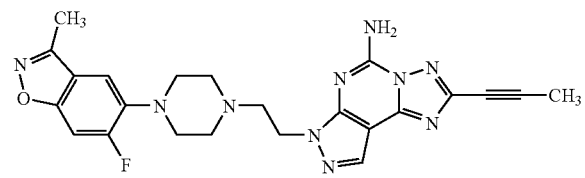

or a pharmaceutically acceptable salt thereof, and 1 to 3 other agents useful in treating Parkinson's Disease.

4. The method of claim 3 wherein the other agents are selected from the group consisting of L-DOPA, dopaminergic agonists, MAO-B inhibitors, DOPA decarboxylase inhibitors and COMT inhibitors.

5. The method of claim 1 for treating or preventing Extra-Pyramidal Syndrome.

6. The method of claim 5 wherein the Extra-Pyramidal Syndrome has been caused by treatment with a typical antipsychotic agent or an atypical antipsychotic agent.

7. The method of claim 6 wherein the typical antipsychotic agent is selected from the group consisting of loxapine, haloperidol, chlorpromazine, prochlorperazine and thiothixene, and the atypical antipsychotic agent is selected from the group consisting of clozapine, olanzapine, loxapine, quetiapine, ziprasidone, risperidone and aripiprazole.

8. The method of claim 5 further comprising administering an antipsychotic agent.

9. The method of claim 8 wherein the antipsychotic agent is a typical antipsychotic agent selected from the group consisting of loxapine, haloperidol, chlorpromazine, prochlorperazine and thiothixene, or an atypical antipsychotic agent selected from the group consisting of clozapine, olanzapine, loxapine, quetiapine, ziprasidone, risperidone and aripiprazole.

10. A method of claim 1 for the treatment of idiopathic dystonia or dystonia caused by the use of cocaine.

11. The method of claim 1 for the treatment or prevention of dystonia caused by treatment with a tricyclic antidepressant, lithium or an anticonvulsant.

12. The method of claim 11 further comprising administering a tricyclic antidepressant, lithium or an anticonvulsant.

13. The method of claim 12 wherein the tricyclic antidepressant is selected from the group consisting of perphenazine, amitriptyline, desipramine, doxepin, trimipramine and protriptyline, and the anticonvulsant is selected from the group consisting of phenytoin, carbamazepine and gabapentin.

14. A method of treating restless leg syndrome or periodic leg movement in sleep comprising administering a therapeutically effective amount of a compound of the formula

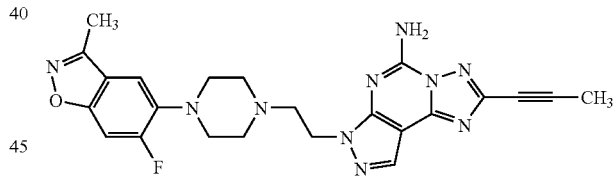

or a pharmaceutically acceptable salt thereof to a patient in need thereof.

15. The method of claim 11 further comprising administering levodopa/carbidopa, levodopa/benserazide, a dopamine agonist, a benzodiazepine, an opioid, an anticonvulsant or iron.

* * * * *